United States Patent
Giri et al.

(10) Patent No.: US 10,059,924 B2
(45) Date of Patent: Aug. 28, 2018

(54) CLERODENDRUM VISCOSUM AND METHODS OF USE

(71) Applicant: The City University of New York, New York, NY (US)

(72) Inventors: Swami Nirmalananda Giri, Palghat District (IN); Krishnaswami Raja, Staten Island, NY (US); Jimmie Fata, Staten Island, NY (US); Chong Sun, Nanchang (CN); Rema Balambika, Staten Island, NY (US); David Bolton, Staten Island, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 398 days.

(21) Appl. No.: 14/079,250

(22) Filed: Nov. 13, 2013

(65) Prior Publication Data
US 2014/0134731 A1 May 15, 2014

Related U.S. Application Data (60) Provisional application No. 61/725,822, filed on Nov. 13, 2012.

(51) Int. Cl.
*C12N 5/09* (2010.01)

(52) U.S. Cl.
CPC ........ *C12N 5/0693* (2013.01); *C12N 2500/76* (2013.01)

(58) Field of Classification Search
CPC .......................... C12N 5/0693; C12N 2500/76
See application file for complete search history.

(56) References Cited

PUBLICATIONS

Elmore (2007). Apoptosis: A Review of Programmed Cell Death. Toxicologic Pathology, v35(4), p. 495-516.*

Bhatnagar and Pattanaik (May 2012). Comparative Analysis of Cytotoxic and Antioxidant Activities of Leaf and Bark Extracts of Clerodenrum Viscosum and Clerodendrum Phlomidis. International Journal of Biomedical and Advance Research, v3(5), p. 385-390.*
Das et al. (2010). Anticancer Activity of Clerodendron infortunatum Linn. Extract in Swiss Albino Mice. Asian J. Chem, v22(8), p. 6387-6392.*
Govaerts, R. (1999 or 2003). World Checklist of Selected Plant Families Database in ACCESS: 1-216203. The Board of Trustees of the Royal Botanic Gardens, Kew.*
Prakash et al. (2011). Antioxidant activity of ethanolic extracts of Clerodendrum viscosum vent and Biophytum condolleanum wight. Der Pharmacia Lettre, v3(4), p. 248-251.*
Wingfeld (1998). Protein Precipitation Using Ammonium Sulfate. Current Protocols in Protein Science, supplement 13, A.3F1-A.3F.8.*
Liu et al. (2008). Preparation of Botanical Samples for Biomedical Research. Endocr Metab Immune Disord Drug Targets, v8(2): 112-121.*
Burdick and Jackson Solvents—Polarity Index (2004). 2 pages.*
Fulda et al. (2000). Caspase Activation in Cancer Therapy. Landes Bioscience, 12 pages.*
Koff (2015). A Time to Kill: Targeting Apoptosis in Cancer. Int. J. Mol. Sci. v16, p. 2942-2955.*
Hague et al. Evaluation of antitumor activity of some medicinal plants of Bangladesh by potato disk bioassay. Fitoterapia (2000), v71, p. 547-552.*

\* cited by examiner

*Primary Examiner* — Sean C. Barron
(74) *Attorney, Agent, or Firm* — Hoffmann & Baron, LLP (57) ABSTRACT

The present invention provides for a composition and formulations comprising an extract from *Clerodendrum viscosum*, and a method of obtaining the extract. The present invention also provides for a method of treating any disease where uncontrolled cellular proliferation occurs, such as cancers. In particular, the present invention provides a method for treating cervical cancer. The present invention also provides methods to inhibit proliferation and induce apoptosis of cancer cells.

7 Claims, 9 Drawing Sheets

CLERODENDRUM VISCOSUM AND METHODS OF USE

BACKGROUND

Cervical cancer is the second most common cancer worldwide, which causes about 275,000 deaths annually (Parkin D M.; Bray F.; Ferlay J.; Pisani P. Global cancer statistics, 2002. CA cancer J Clin, 2005; 55:74-108). It is estimated that 70% of the cervical cancer is caused by the Human papillomavirus (HPV): Cervical cancer can be detected via the Pap test. HPV vaccines have been licensed in the USA, Canada, Australia and EU. In the United States, FDA has approved HPV two vaccines, Human Papillomavirus Quadrivalent (Types 6, 11, 16, 18) Vaccine, Human Papillomavirus Bivalent (Types 16, 18) Vaccine (Vaccines Licensed for Immunization and Distribution in the US with Supporting Documents. U.S. Food and Drug Administration. 2009). Despite the fact that cervical cancer can be dramatically reduced by the cervical screen and vaccination, the mortality rate in the United States was 2 deaths per 100,000 women per year for the period from 2003 through 2007 (NIH). In 2010, an estimated 12,200 women in the United States will be diagnosed with cervical cancer, and an estimated 4,210 will die of the disease (Cancer Advances In Focus: Cervical Cancer. National Cancer Institute. The incidence of invasive cervical cancer has remained stable in industrialized nations. In developing countries, cervical cancer is the most common cancer and the leading cause of the cancer death among women. It is estimated that 200,000-300,000 women die from cervical cancer every year, mostly in the third world (World Health Organization).

Currently, chemotherapy and radiation are the major therapies for the treatment of cancer. However, the side-effect of the chemotherapy and radiation is unavoidable as it indiscriminately kills all fast-growing cells. Hence there exists a long standing need to provide a cancer therapeutic agent that does not harm healthy cells and is specific for cancerous cells, as well as being easily manufactured or produced.

SUMMARY OF THE INVENTION

The present invention provides a composition having an extract from *Clerodendrum viscosum*, and a method of obtaining the extract.

The present invention also provides for a method of treating cancer by administering a composition having an extract of *Clerodendrum viscosum* to a person in need thereof.

The present invention also provides for a method of activating caspase-3 in a cell by administering a composition having an extract of *Clerodendrum viscosum* to a cell.

The present invention also provides for a method of inducing apoptosis in a cell by administering a composition having an extract of *Clerodendrum viscosum* to a cell.

BRIEF DESCRIPTION OF THE DRAWINGS

FIG. 2A depicts a schematic diagram showing the method for the isolation of active fractions from Cv-AP. The components of Cv-AP were separated on a Superdex 200 column, and four populations of substances were eluted off, termed P1-P4. The yield percent of P3 is 30.87%. P3 was heated at 95° C. for 1 hour, and centrifuged at 12,000 for 5 min. The resulting supernatant is HP3, and the pellet is HPP3. The Yield percent of HP3 is 22.81%. Ethanol was added HP3 to a final ethanol concentration of 66%, the ethanol mixture was incubated at −20° C. overnight and centrifuged at 12,000 RPM for 5 min. The resulting pellet is EPHP3 with a yield percent of 2.87%, and the supernatant is ESHP3 with a yield percent of 10.63%.

(FIG. 4A) SDS-PAGE of Cv-AP reveals prominent bands around 18 kDa when stained with Coomassie blue (lane 1). The two most prominent bands stain positive with Pro-Q emerald 300, a dye which selectively stains glycoproteins. These glycoproteins are not present if Cv-AP is pretreated with proteinase-K prior to loading and staining with Pro-Q (lane 3). (FIG. 4B) The UV-Vis spectrum of the Cv-AP-Concanavalin A (Con. A), the presence of large cross linked aggregates (Tyndall scattering) confirms the presence of glycoproteins in the Cv-AP extract. Glucose was used to break and dissolve the cross linked aggregate between the Con. A and Cv-AP by competitively displacing Cv-AP from Con. A.

(FIG. 5A) HeLa cells treated with media alone, Cv-AP (0.01 mg/ml), or Cv-AP (0.1 mg/ml) were assayed to determine the amount of cells at 1 day, 2 day, and 3 days using a WST-1 assay. Percent proliferation was determined by setting day 3 media alone to 100%. The WST-1 assay revealed that HeLa cells exhibited a dose-dependent inhibition of proliferation when exposed to Cv-AP. (FIG. 5B) At higher concentrations, Cv-AP (1.25 mg/ml) drastically reduces the percentage of cells immune-positive for the proliferation marker Phospho-Histone-3. Scale bar in A=0.2 mm.

(FIG. 6A) HeLa cells were untreated or treated with 0.63 mg/ml CV-AP. Individual cell movement was tracked in real time over 24 hours by time-lapsed microscopy (30 minute intervals) and celltrack software. The path of a cell is depicted by a line connecting the two circles. Cells treated with 0.63 mg/ml of Cv-AP failed to migrate any distances, whereas untreated cells showed significant migration (FIG. 6B) Cells exhibited membrane ruffling (arrows) at the migratory leading edge when untreated. These morphologies were not evident in any cell treated with Cv-AP. (FIG. 6C) Quantification of cell migration revealed a significant inhibition by 0.63 mg/ml Cv-AP when compared to untreated cells (*=p<0.05). Scale bar in A=0.2 mm, B=0.03 mm.

(FIG. 7A) HeLa cells were treated with 0 (untreated), 2.5, 5, or 10 mg/ml Cv-AP for 6 hrs. The cells were then fixed, and immunostained for tubulin. The panels show a dose dependent disruption of tubulin structure. (FIG. 7B) HeLa cells were treated with 10 mg/ml Cv-AP for 6 hrs and fractionated into soluble and insoluble material. Immunoblot detection of tubulin indicated Cv-AP (10 mg/ml) decreased both the total amount of tubulin and the insoluble fraction, when compared to media alone (Untreated). (FIG. 7C) The results of panel B were quantified to show that the Cv-AP significantly reduced the amount of insoluble/soluble tubulin in HeLa cells after 6 hrs of treatment (*=p<0.05). Scale bar in A=0.05 mm.

(FIG. 8A) Time lapse imaging of HeLa cells treated with Cv-AP (10 mg/ml) along with propidium iodide (PI) for 7 hours. Brightfield (upper panels) and fluorescent images (bottom panels) at two hour intervals reveal cell shrinking, membrane blebbing, and PI fluorescence is evident by 7 hrs. A PI positive nucleus indicates cell death by staining cells whose membranes have been compromised. (FIG. 8B) HeLa cells were treated for 8 hours with increasing concentration of Cv-AP (0.16 mg/ml, 0.31 mg/ml, 0.63 mg/ml, 1.25 mg/ml, 2.5 mg/ml and 5 mg/ml) were scored for percentage of PI positive cells to determine the dose that kills 50% of the cells (LD50). (FIG. 8C) Cell death induced by Cv-AP was confirmed to be apoptosis by immune-detection of cleaved caspase-3 after treated with 10 mg/ml CV-AP after 7 hr. HeLa cells treated with TNFα plus cyclohexamide were used as a positive control. (FIG. 8D) At 7 hours almost all HeLa cells treated with 10 mg/ml are dead (PI positive; top panels), whereas under the same conditions, primary normal human fibroblasts show no Cv-AP-induced cell death (bottom panels). Scale bars in A=16 μm, B=0.2 mm, C=0.2 mm.

DETAILED DESCRIPTION

The present invention provides a composition having an extract from *Clerodendrum viscosum*, and a method of obtaining the extract. The present invention also provides for a method of treating cancer by administering a composition having an extract of *Clerodendrum viscosum* to a person in need thereof. The invention also provides a method for activating caspase-3 in a cell by administering the composition to the cell. The invention also provides a method of inducing apoptosis in a cell by administering the composition to the cell.

Composition

In one aspect, the invention provides a composition having an extract from *Clerodendrum viscosum*. The extract may be obtained using any method known to a person skilled in the art. Some non-limiting examples of obtaining extracts include solvent extraction, hot continuous extraction, decoction, or percolation.

The extract may be prepared from any portion of the *Clerodendrum viscosum* plant. In a preferred embodiment, the extract from *Clerodendrum viscosum* is prepared from the roots.

For example, the extract of the present invention may be obtained by solvent extraction. Solvent extraction is a method well known in the art, especially in relation to the production of plant extracts. Solvent extraction generally involves macerating, chopping up into small pieces, or otherwise breaking down the raw plant material and then adding one or more solvents to the plant material for a period of time to allow the active ingredient(s) in the plant material to be captured in the solvent. The solvent containing the active ingredient(s) is then separated from the plant product, optionally by filtration, and the solvent is removed by evaporation or other means, leaving the plant extract with desired phyto-chemical and pharmacological activity.

In one embodiment, the extract is obtained by first adding a solvent to *Clerodendrum viscosum*, followed by homogenization to create a suspension. Any suitable solvent may be used. Examples of suitable solvents include water, aqueous buffer, or organic solvents. The water may be distilled or deionized. Any aqueous buffer compatible with the extract may be used as the solvent. Examples of suitable aqueous buffers include phosphate buffered saline (PBS) or TRIS based buffers. The solvent may be an organic solvent. Examples of suitable organic solvents include dimethyl sulfoxide (DMSO), methylsulfonylmethane (MSM), ethanol, chloroform, hexane, tetrahydrofuran, dioxane, petroleum ether, dichloromethane, diethyl ether, toluene, digol, methanol, ethyl acetate, isopropanol, tertiary butyl alcohol, dimethyl formamide, N-methylpyrollidone, and other water miscible and immiscible solvents. Solvents can be used individually, or in combination.

The *Clerodendrum viscosum* and solvent mixture, as described above, may be homogenized by any known method. For example, a blender, or mortar and pestle can be used to homogenize the plant solvent mixture.

The resulting homogenized suspension is diluted with a solvent, and stirred under inert gas (e.g. nitrogen or argon) for 10-40 hours at a temperature between 37° C. and 100° C. Preferably, the suspension is stirred for 24 hours at a temperature of 80° C. The suspension is then filtered and the liquid extract is lyophilized to produce a white/off white product that is the extract. Methods of filtration and lyophilization are generally known by those of ordinary skill in the art.

In another embodiment, the *Clerodendrum viscosum* extract is obtained from dried plants, in whole or in part. Once dried, the plant material can be further processed, e.g. suspending, homogenizing, and removal by filtration and/or centrifugation. *Clerodendrum viscosum* plants can be dried by any known means. For example, the *Clerodendrum viscosum* may be dried at a temperature between 25° C. and 45° C. for 1-10 hours. Preferably, the *Clerodendrum viscosum* is dried for 3 hours at 37° C.

Solvent, as described above, can then be added to the dried *Clerodendrum viscosum*, and the combination is then homogenized, yielding a suspension. The homogenized suspension is incubated at a temperature between 1° C. and 20° C., with stirring, for 8-48 hours. Preferably, the incubation and stirring occurs at 4° C. for 24 hours. The stirring may occur under inert gas. The insoluble plant residue may be removed by centrifugation and/or filtration. For example, the suspension may be centrifuged at 15,000 RPM for 15 minutes. Any type of filtration known in the art may be used to remove particulate matter. Preferably, the supernatant is filtered through a membrane having 0.22 μm pores.

Optionally, before the next step, the supernatant may be further clarified. For example the supernatant may be treated with solid ammonium sulfate to 40% saturation and stirred at 4° C. for 8-24 hours. The supernatant from this step is then used in the next step.

The supernatant, as described above is treated with solid ammonium sulfate to 80% saturation and stirred at 4° C. overnight, yielding a precipitate. The precipitate is collected by centrifugation at 3,000 RPM for 15 minutes and dissolved in distilled water. The solution of dissolved precipitate is then centrifuged at 16,000 RPM for 20 minutes to remove insoluble material, and the supernatant is lyophilized to yield a substance that is the extract.

The extract may be further processed to increase the purity and remove any contaminants that may interfere with activity or incompatible for use in humans. For example, the extract as described above is incubated at 95° C. for 1 hour, and centrifuged at 12,000 RPM for 5 min. The supernatant is then isolated and ethanol added to a final concentration of 66%. The solution is then incubated at −20° C. overnight.

The solution is then centrifuged at 12,000 RPM for 5 min. The resulting pellet is then isolated, and contains the purified extract.

In a preferred embodiment, the extract may be further purified by chromatography. Examples of suitable chromatography methods include ion exchange, molecular exclusion, hydrophobic interaction, or reverse-phase chromatography. Furthermore, automated chromatography systems may be used. Examples of automated chromatography systems include fast performance liquid chromatography (FPLC), and high pressure liquid chromatography (HPLC).

In a preferred embodiment, the invention provides an extract from *Clerodendrum viscosum* comprising a glycoprotein having a molecular weight in the range between 15 kDa and 25 kDa. Preferably, the glycoprotein has a molecular weight of about 18 kDa. See FIGS. 2A-2D and FIGS. 4A-4B. In another preferred embodiment, the glycoprotein has terminal α-D-mannosyl and α-D-glucosyl groups.

Methods of Use

In another aspect, the present invention provides for methods to treat any disease where uncontrolled cellular proliferation occurs, such as cancers. The composition, as described above, can be active against one or multiple pathways implicated in cancer. In a preferred embodiment, the method includes administration of the composition described above to inhibit cancer cell proliferation.

The type of cancer applicable to the instant invention is not particularly limited. The composition, formulations, and methods disclosed herein can be applied to solid cancer, blood cell cancer, and the like. Among these cancers, the solid cancer is a preferable subject to which the invention is applicable.

A non-limiting list of cancers as applicable to the instant invention include glioblastoma, medulloblastoma, leukemia, Hodgkin's lymphoma, non-Hodgkin's lymphoma, carcinoma, sarcoma, myeloma, prostate cancer, bladder cancer, breast cancer, kidney cancer, pancreatic cancer, anal cancer, oseophegal cancer, colon cancer, skin cancer, biliary cancer, stomach cancer, head and neck cancer, solid carcinoma, squamous cell carcinoma, adenocarcinoma, glioma, high grade glioma, blastoma, neuroblastoma, plasmacytoma, histiocytoma, melanoma, adenoma, hypoxic tumor, myeloma, AIDS-related lymphoma or AIDS-related sarcoma, or metastatic cancer, B cell lymphoma, T cell lymphoma, mycosis fungoides, Hodgkin's Disease, myeloid leukemia, brain cancer, nervous system cancer, squamous cell carcinoma of head and neck, lung cancer, small cell lung cancer, non-small cell lung cancer, ovarian cancer, pancreatic cancer, prostate cancer, skin cancer, liver cancer, melanoma, squamous cell carcinoma of the mouth, squamous cell carcinoma of the throat, squamous cell carcinoma of the larynx, squamous cell carcinoma of the lung, colon cancer, cervical cancer, cervical carcinoma, uterine sarcoma, urethral cancer, endometrial uterine cancer, vaginal cancer, vulvar cancer, epithelial cancer, renal cancer, genitourinary cancer, pulmonary cancer, esophageal carcinoma, large bowel cancer, hematopoietic cancer, testicular cancer, rectal cancer, prostatic cancer, or pancreatic cancer.

In a preferred embodiment, the cancer is cervical cancer.

The composition, formulations, and methods disclosed herein may also be used for the treatment of precancer conditions such as cervical and anal dysplasias, other dysplasias, severe dysplasias, hyperplasias, atypical hyperplasias, and neoplasias. The composition or formulations, may also be administered prophylactically to subjects who are at risk for a cancer as described herein.

Without being bound by theory, it is believed that the composition of the present invention affects a mechanism of apoptosis, whereby apoptosis is mediated by the activation or increased expression of caspases, a family of intracellular cysteine proteases. In particular, the mechanism includes activation or increased expression of caspase-3. Accordingly, in another aspect, the invention provides a method of activating caspase-3 in a cell by administering the composition described herein. In another aspect, the invention includes inducing apoptosis in a cell by administering the composition described herein.

Methods may be carried out by the procedures described herein, or modification thereof which will be apparent to one skilled in the art.

In another embodiment, the composition as described above is administered alone or in conjunction with radiation or chemotherapeutic agents or surgical excision of the involved cells or lesions.

Preferable examples of the chemotherapeutic agent in the present invention include a cancerocidal agent, an anticancer agent or an antitumor agent (hereinafter referred to collectively as anticancer agent), and specifically the anticancer agent includes bleomycin and derivatives thereof, anthraquinone-based cancerocidal agents including adriamycin and daunomycin, mitomycin and derivatives thereof, actinomycin and derivatives thereof, taxane derivatives such as taxol, bevacizumab and derivatives thereof, topotecan and derivatives thereof, camptothecin and derivatives thereof such as irinotecan, cisplatin and derivatives thereof, vinorelbine and derivatives thereof, pemetrexed and derivatives thereof, staurosporine and derivatives thereof, vincristine, streptozotocin, 5-fluorouracil (5-FU) and derivatives thereof, viralbicin and dolastatin, as well as pharmacologically acceptable salts thereof.

The compositions or formulations of the instant invention may be administered in a number of ways depending on whether local or systemic treatment is desired, and on the area to be treated. The therapeutic agent can be provided in any suitable form, generally depending upon the desired administration route. For example, the therapeutic agent can be provided as a salt, a solid, a liquid, a suspension, an aggregate, or a gel. The active compound may be administered in a convenient manner such as by the oral, intravenous (where water soluble), ophthalmic, vaginal, by inhalation, intraperitoneal, intracavity, transdermally intramuscular, intravenous, intranasal, intradermal, subcutaneous, or suppository routes. Depending on the route of administration, the active ingredients of the composition of the invention as described above containing pharmaceutical composition may be required to be coated in a material to protect said ingredients from the action of enzymes, acids or other natural conditions. Furthermore, strategies such as chemical modification, formulation vehicles and use of enzyme inhibitors, absorption enhancers and mucoadhesive polymers may be used.

The method of the invention includes administering an effective amount of the composition to the human in need thereof. An effective amount is defined as an amount sufficient to achieve a beneficial outcome. In particular, an effective amount may be an amount sufficient to reduce, prevent, or inhibit the growth or proliferation of, cancer cells in a human.

In a preferred embodiment, the effective amount is from about 1 μg to about 2000 μg per kg of body weight per day. The dosage regimen may be adjusted to provide the optimum therapeutic response. For example, several divided doses may be administered daily or the dose may be proportionally reduced as indicated by the exigencies of the therapeutic situation.

The compositions and formulations according to the instant invention may include carriers, thickeners, diluents, buffers, preservatives, surface active agents and the like in addition to the delivery vehicle and/or the therapeutic agent. Pharmaceutical compositions may also include one or more active ingredients such as antimicrobial agents, anti-inflammatory agents, anesthetics, and the like.

In certain aspects, compositions and formulations of the present teachings can be delivered to the affected area of the skin in a pharmaceutically acceptable topical carrier. As used herein, a pharmaceutically acceptable topical carrier can be any pharmaceutically acceptable formulation that can be applied to the skin surface for topical, dermal, intradermal, or transdermal delivery of a pharmaceutical or medicament. The combination of a pharmaceutically acceptable topical carrier and a compound of the invention is termed a topical formulation of the invention. Topical formulations of the invention can be prepared by mixing a compound of the invention with a topical carrier according to well-known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

A topical carrier useful for topical delivery of compositions and formulations of the invention can be any carrier known in the art for topically administered pharmaceuticals, for example, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions, such as standard ophthalmic preparations.

The active compositions and formulations may also be administered parenterally or intraperitoneally. Dispersions may also be prepared in glycerol, liquid polyethylene glycols, and mixtures thereof and in oils. Under ordinary conditions of storage and use, these preparations contain a preservative to prevent the growth of microorganisms.

The compositions and formulations according to the instant invention suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (for example, glycerol, propylene glycol, and polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. The preventions of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions may be brought about by the use in the compositions of agents delaying absorption, for example, aluminum monostearate and gelatin.

Sterile injectable solutions are prepared by incorporating the active compositions and formulations in the required amount in the appropriate solvent with various of the other ingredients enumerated above, as required, followed by filter sterilization. Generally, dispersions are prepared by incorporating the various sterilized active ingredients into sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

It is especially advantageous to formulate parenteral compositions in dosage unit form for ease of administration and uniformity of dosage. Unit dosage form as used herein refers to physically discrete units suited as unitary dosages for a person in need thereof to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The compositions and formulations of the invention as described above may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active compound. The percentage of the compositions and preparations may, of course, be varied and may conveniently be between about 5 to about 80% of the weight of the unit. The amount of active compound in such therapeutically useful compositions is such that a suitable dosage is obtained. A suitable dosage is any dosage sufficient to achieve a beneficial outcome. Preferred compositions or preparations according to the present invention are prepared so that an oral unit dosage form contains between about 10 µg and 1000 µg of active compound.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; a sweetening agent, such as sucrose, lactose or saccharin or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, "about" refers to numeric values whether or not explicitly indicated. The term "about" generally refers to a range of numbers (e.g., +/−5-10% of the recited value) that one would consider equivalent to the recited value (i.e., having the same function or result). In many instances, the term "about" may include numbers that are rounded to the nearest significant figure.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1

Preparation of Standardized Extract from *Clerodendrum Viscosum*

*Clerodendrum viscosum* roots were dried in a vacuum oven at 37° C. for 3 hours. 100 grams of dried root was homogenized with a blender and extracted in 1000 ml PBS (PH=7.4) at 4° C. for 24 hours with stifling. The root residue was removed by centrifugation at 15,000 RPM for 15 minutes and the supernatant was filtered using 0.22 μm filter paper. The filtered fluid was treated with solid ammonium sulfate to 40% saturation and stirred at 4° C. overnight. The supernatant was collected, and ammonium sulfate was added to 80% saturation and stirred at 4° C. overnight. The precipitate was collected by centrifugation at 3,000 RPM for 15 minutes and dissolved in distilled water. The solution was then centrifuged at the 16,000 RPM for 20 minutes to remove the insoluble material, and the supernatant was lyophilized to yield the extract, Cv-AP, which was stored at −20° C.

Example 2

Characterization of *Clerodendrum viscosum* Extract

Figure 3A:
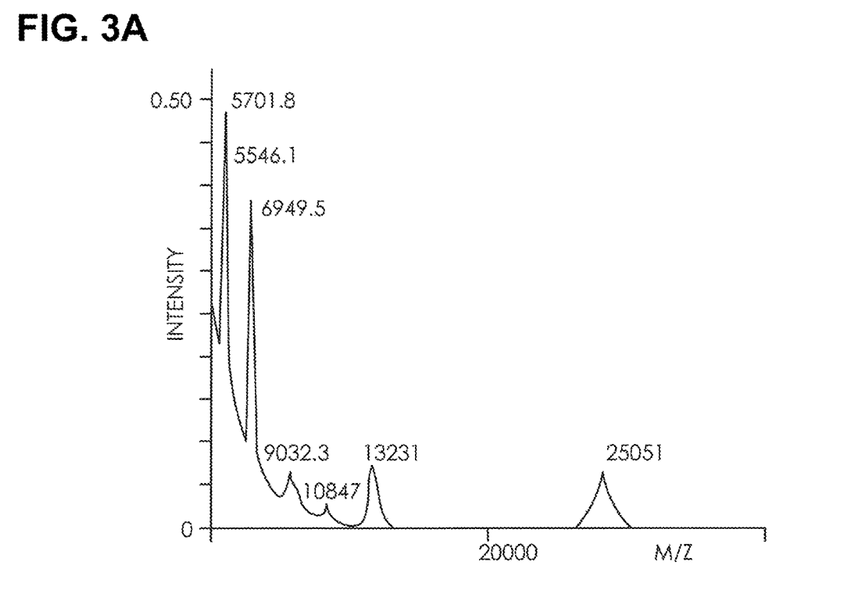
FIGS. 3A-3B depict MALDI TOF data of fractions of (FIG. 3A) Cv-AP and (FIG. 3B) P3.
Figure 3B:
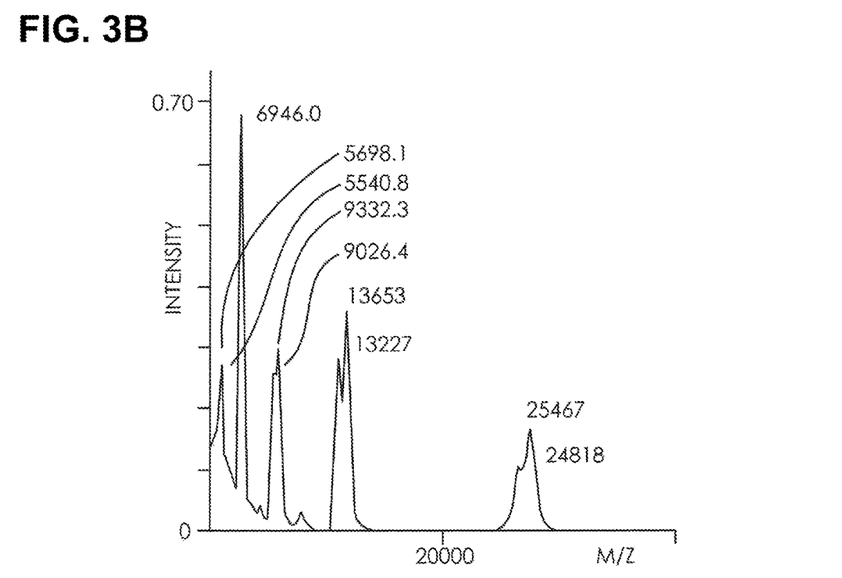
Figure 4A:
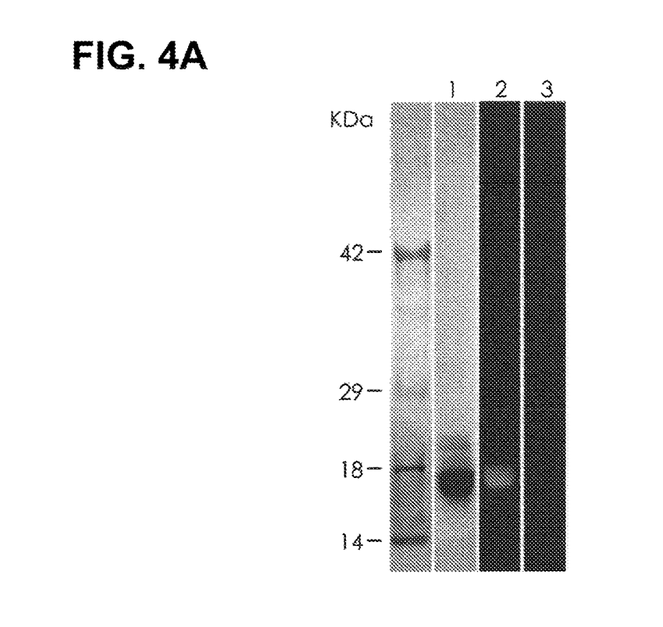
FIGS. 4A-4B depict SDS PAGE and Concavalin A experiments.
Figure 4B:
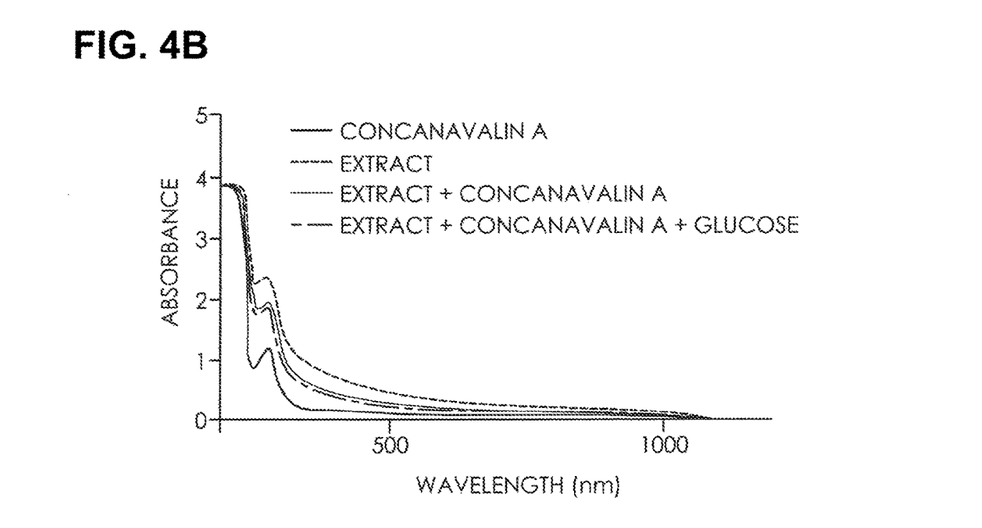

A major protein of ~18 kDa was present in SDS-PAGE analysis of Cv-AP (FIG. 4, Lanes 1 & 2). The molecular weight was estimated using the glycoprotein molecular weight standard kit supplied by Invitrogen (Catalog Number C-21852), the estimated molecular weight is relative. The protein was depolymerized after incubation with proteinase K for 24 h. (FIGS. 3A-3B). Cv-AP stained positive with emerald 300 (FIGS. 4A), indicating Cv-AP that a significant component is a glycoprotein. Cv-AP also stains positive with Coomassie blue confirming that it is a protein. To further confirm the presence of sugars in Cv-AP, Con A binding assay was used. Concanavalin A specifically binds to certain moieties found in various sugars, glycoproteins, and glycolipids, mainly nonreducing terminal α-D-mannosyl and α-D-glucosyl groups (Goldstein I J, Liener I E, Sharon N. The Lectins Properties, Functions and Applications in Biology and Medicine. San Diego: Academic., 1986, pp. 233-247. ISBN 0-12-449945-7). The addition of a Con A solution to Cv-AP results in an increased absorbance throughout the UV spectrum which characteristic of Tyndall scattering resulting from the formation of cross linked aggregates between Con-A and Cv-AP (FIG. 4B). The Con-A-Cv-AP aggregates can be dissolved by the addition of glucose; glucose disrupts the aggregates by competitively displacing Cv-AP (FIG. 4B).

Figure 1:
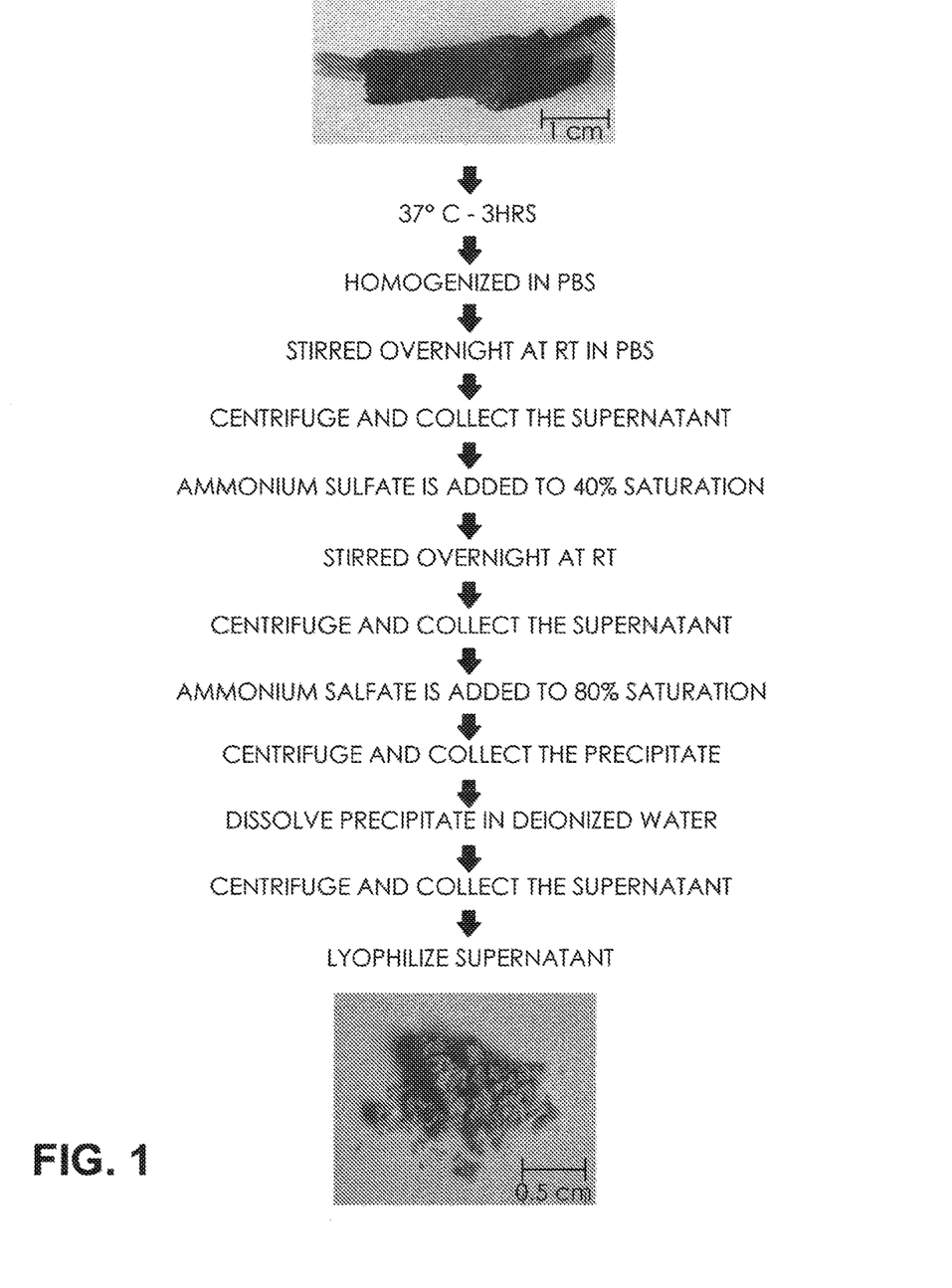
FIG. 1 depicts a schematic summarizing an example of an extraction protocol.
Figure 2A:
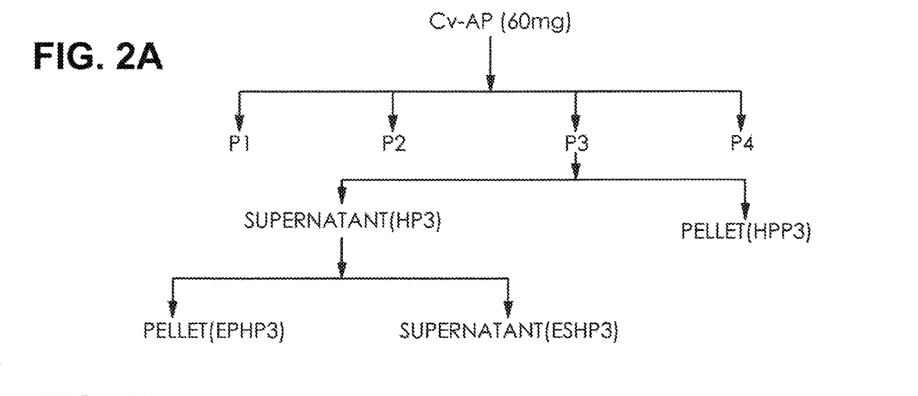
Figure 2B:
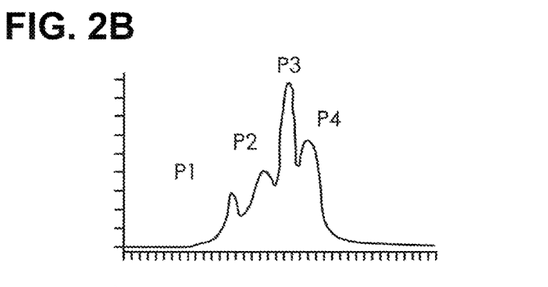
(FIG. 2B) FPLC elution profile for the separation of Cv-AP by GE Healthcare HiPrep Superdex 200 300/10 size exclusion column.

Cv-AP was separated by size exclusion chromatography on a GE Healthcare HiPrep Superdex 200 300/10 size exclusion column (FIGS. 2A-2B). The components of the Cv-AP were tested for activity. See Table 1.

Cv-AP and fractions were redissolved in 0.1% trifluoroacetic acid (TFA) deionized water at the concentration of 2.5 mg/ml. The Stainless steel MALDI sample plate was cleaned with methanol and wiped dry followed with water wash and wiping dry. The cleaning was repeated and dried before use. 30 μl of thin layer substrate solution (1 part of saturated 4-HCCA in TAW (0.1%:2:1) (TFA:ACN:water)+3 parts isopropanol) was applied and spread on the plate. After waiting 5 minutes the excess solution was wiped off. The sample was diluted [1 part into 4 part of matrix solution (saturated 4-HCCA in FWI (3:1:2) (formic acid:water:isopropanol)]. 1 µl sample/matrix mixture was spotted on the plate and waited 5 minutes to see the crystallization form at the interface of matrix and sample. The excess liquid was removed by vacuum aspiration. Each spot was washed with 1 µl of an ice cold 0.1% TFA solution and the excess liquid was removed by vacuum aspiration. MS experiments were performed using a MALDI-time-of-flight mass spectrometer (Bruker Daltonik, Bremen, Germany). The data was analyzed by Moverz bioinformatics software.

MALDI-TOF Analysis

To investigate Cv-AP (standardized extract presented in the paper) and fractions, applicants tested them by MALDI-TOF. The MALDI spectrum of Cv-AP (FIG. 3A) had multiple peaks and the major peak was about 25 kDa, and there were additional peaks as 13 kDa, 9 kDa, and 6 kDa. All these peaks were also observed in the MALDI spectrum of P3 (FIG. 3B).

However, the MALDI spectrum of EPHP3 (highly purified fraction) was a little different compared the spectrum of the Cv-AP and P3 (FIGS. 3A-3B). The MALDI spectrum of the EPHP3 had four peaks at the m/z 69 kDa, 9.2 kDa, 13.5 kDa and 25 kDa which was 3, 4, 6 and 11 times of the number 2,317 Da indicating that they are ions of the same protein with varying charges.

Figure 2C:
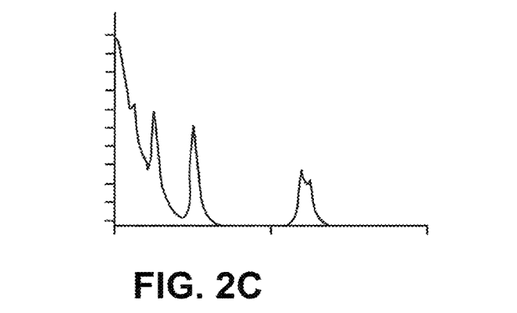
(FIG. 2C) MADI-TOF data of the EPHP3 isolate. m/z peaks were present at 6951.2, 9179.2, 13481, and 25278.
Figure 2D:
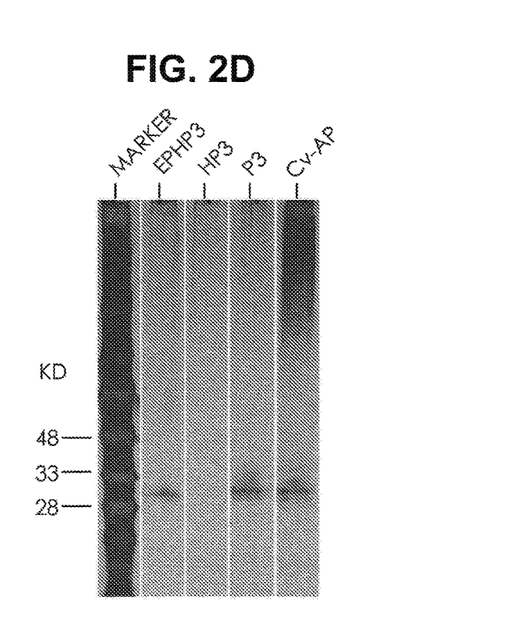
(FIG. 2D) Silver staining gel of the Cv-AP and its fractions on 4-20% gel at different stages of purification, the molecular weight standard is Gentaur RunBlue, catalog number: NXA05160.

Cv-AP and P3 had some other additional compounds in their MALDI-TOF (FIG. 3) spectra although they have the similar major peaks as the MALDI of EPHP3 (FIG. 2C). These small peaks indicated that there were some other compounds in the Cv-AP and P3. EPHP3 had four peaks at the m/z 6.9 kDa, 9.2 kDa, 13.5 kDa and 25 kDa which was 3, 4, 6 and 11 times of the number 2317 Da indicating that they are ions of the same protein with varying charges indicating that the sample is of well-defined purity.

Example 3

*Clerodendrum viscosum* Extract Inhibits the Proliferation of HELA Cells

To estimate the anti-cancer ability of the Cv-AP, applicants first tested the effect of Cv-AP on HeLa cell proliferation. WST-1 assay and immunofluorescence staining were used to evaluate proliferating cell population.

Figure 5A:
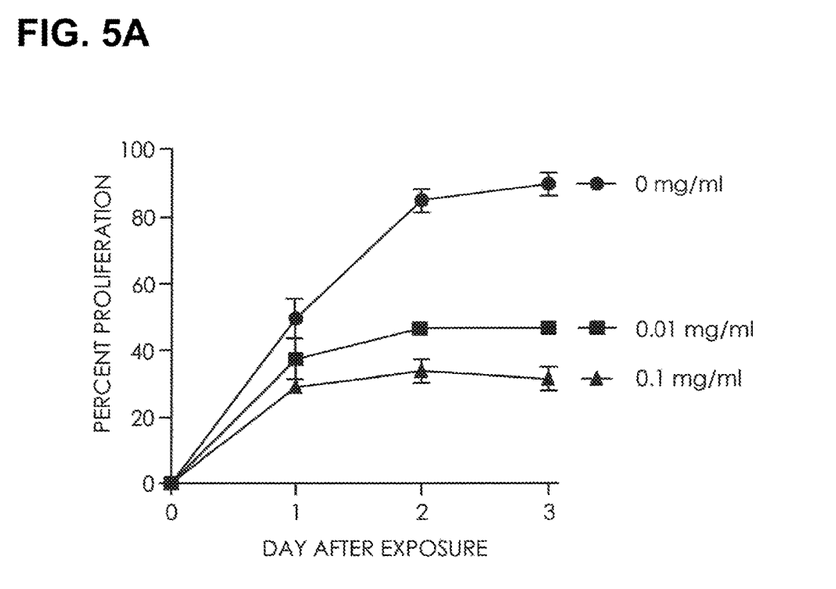
FIGS. 5A-5B depict the effect of Cv-AP on the proliferation of HeLa cells.
Figure 5B:
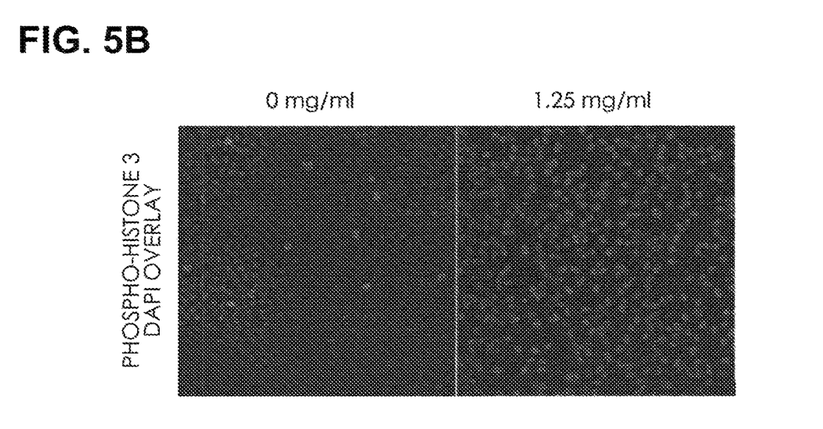

HeLa cells were incubated with 0.1 mg/ml and 0.01 mg/ml concentration of Cv-AP and compared with the HeLa cells without treatment for 72 h. The results from the WST-1 assay indicated the proliferation of HeLa cells was inhibited by the Cv-AP (>50% inhibition). The proliferation of cancer cells decreased with the increasing concentration of Cv-AP (FIGS. 5A-5B).

Given the finding that the Cv-AP can inhibit the proliferation of the HeLa cells, applicants next measured the HeLa cells proliferation by Phospho-Histone3 (pH3) staining to confirm the Cv-AP inhibited HeLa cell proliferation. HeLa cells were treated with or without 1.25 mg/ml Cv-AP for 24 h and stained with anti-phospho histone3 antibody, which exclusively stained the mitotic cells. pH3 phosphorylation can be directly correlated with cell proliferation and can be used as a marker of the proliferation (Kuramitsu K.; Gallo D.; Yoon M.; Chin B Y.; Csizmadia E.; Hanto D W.; Otterbein L E. Carbon monoxide enhances early liver regeneration in mice after hepatectomy. Hepatology. 2011; 53(6): 2016-26.). The number of pH3-positive HeLa cells in the Cv-AP treated sample was much less than the control HeLa cells (FIGS. 5A-5B).

Example 4

*Clerodendrum viscosum* Extract Inhibits the Motility of HELA Cells

Figure 6A:
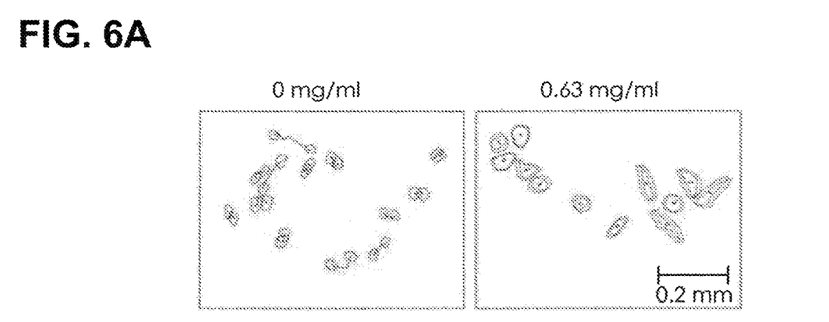
FIGS. 6A-6C depict the effect of Cv-AP on the motility of HeLa cells.
Figure 6B:
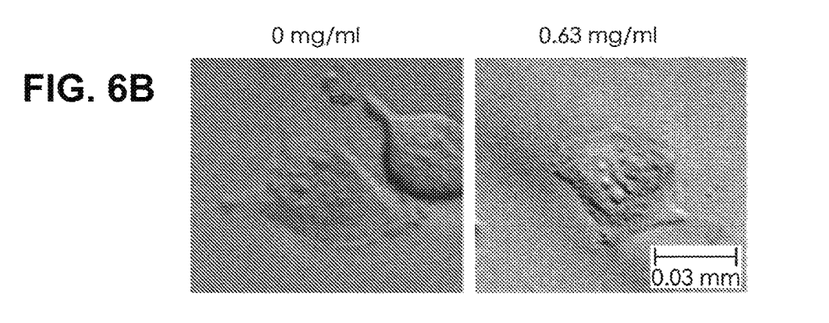
Figure 6C:
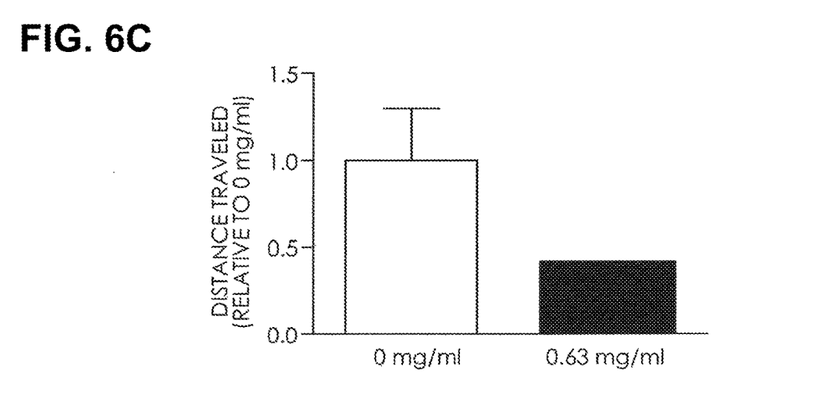

To test the effect Cv-AP on cancer cell motility, applicants tested a lower concentration (0.63 mg/ml) of Cv-AP was used on HeLa cells to avoid killing the cells. Time-lapsed microscopy was used to record the movement of the cells in real time for 24 hours (30 minutes intervals) (FIGS. 6A-6C). Applicants observed that HeLa cells treated with Cv-AP lost mobility and were essentially frozen at the initial position (FIGS. 6A-6C). Cv-AP impaired HeLa cells motility by 60% compare to control HeLa cells without treatment (FIGS. 6A-6C); Cv-AP significantly reduces cell motility ($p<0.05$).

Example 5

*Clerodendrum viscosum* Extract Alters Tubulin Structure HELA Cells

Figure 7A:
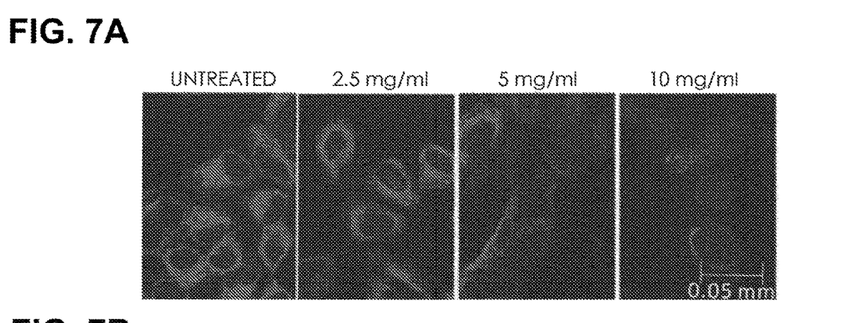
FIGS. 7A-7C depict the effect of Cv-AP on tubulin structure.
Figure 7B:
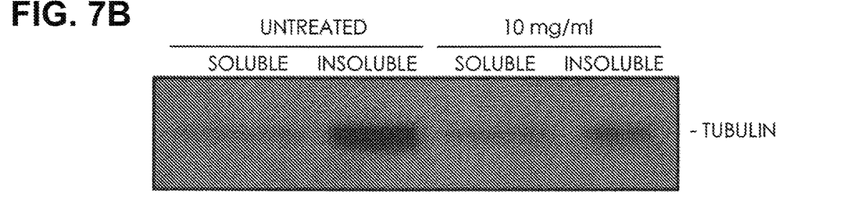
Figure 7C:
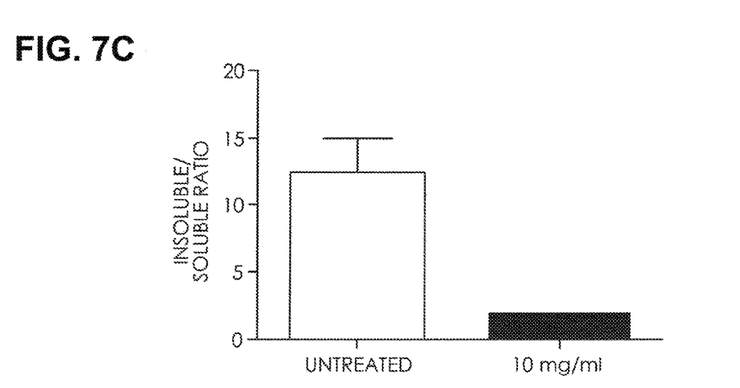
Figure 8A:
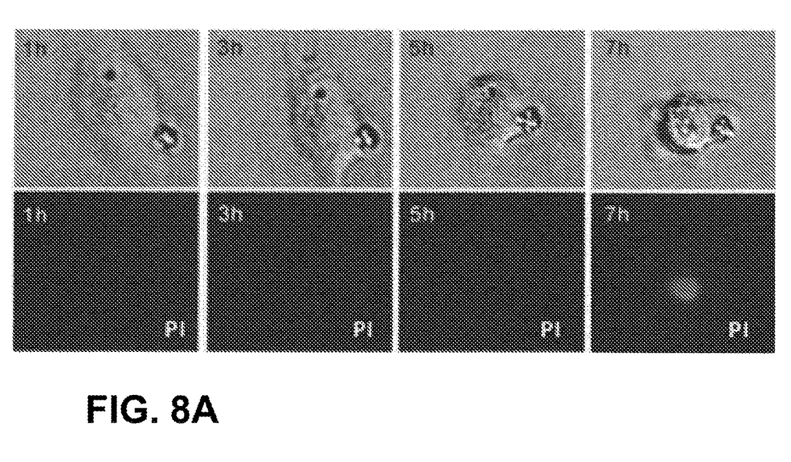
FIGS. 8A-8D depict the effect of Cv-AP on cell death and apoptosis of HeLa cells.
Figure 8B:
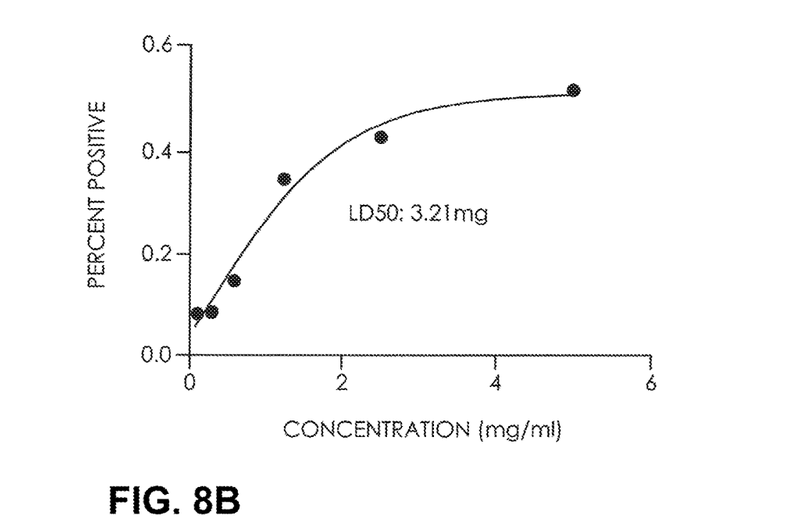
Figure 8C:
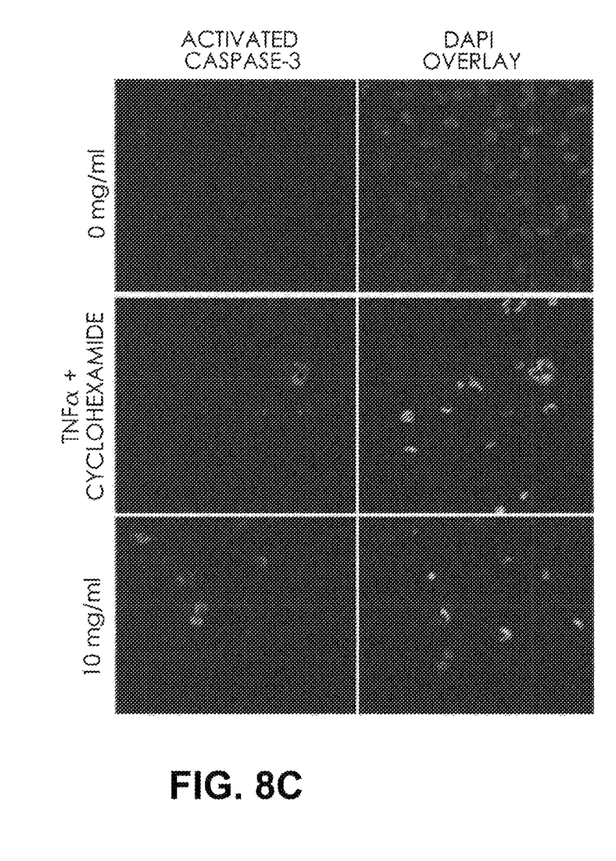
Figure 8D:
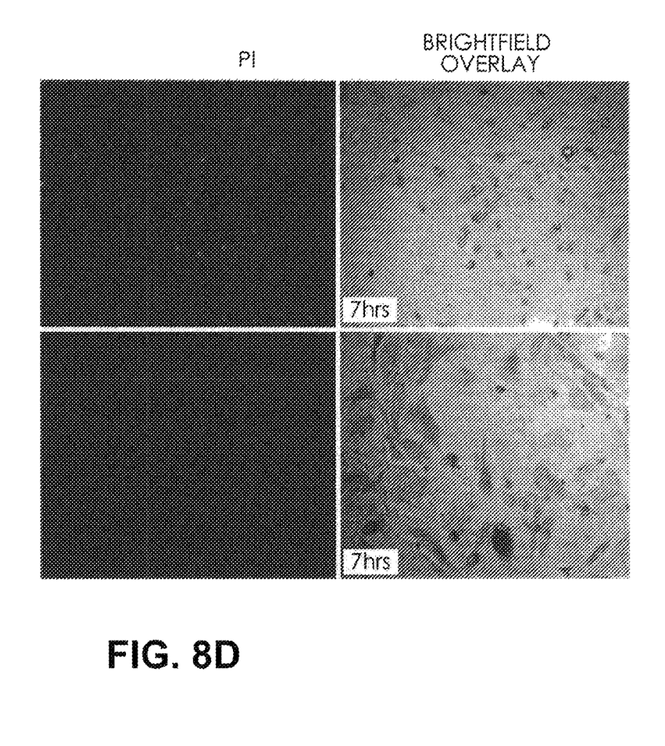

Cell motility is a complex process requiring coordinated organization of actin and microtubules cytoskeletons in physiological and pathological conditions (Sanhaji M.; Friel C T.; Wordeman L.; Louwen F.; Yuan J. Mitotic centromere-associated kinesin (MCAK): a potential cancer drug target. Oncotarget. 2011; 2(12):935-47). Since Cv-AP can reduce HeLa cells motility, it is important to unravel the mechanism of action of Cv-AP on altering the motility of cancer cells. Applicants measured the organization of tubulin on the HeLa cells after treatment with Cv-AP for 6 hrs. Three different concentrations Cv-AP (2.5, 5 and 10 mg/ml) were employed to treat HeLa cells, followed by staining with anti-tubulin antibody. Increased concentration of Cv-AP resulted in increased tubulin disassembly (FIGS. 7A-7C). Given the fact that Cv-AP disassembled tubulin, applicants estimated the insoluble-to soluble tubulin ratio. HeLa cells were treated with 10 mg/ml Cv-AP for 5 hrs and insoluble and soluble tubulin fractions were separated and immunoblotted for tubulin (FIG. 7B) and quantified by software ImageJ (FIG. 7C). HeLa cells without treatment with Cv-AP were used as control. It is clear from FIGS. 7A-7C that control HeLa cells have more filamentous tubulin compared to HeLa cells treated with Cv-AP after 5 hrs, and the difference is statistically significant ($P<0.05$).

Example 6

*Clerodendrum viscosum* Extract Induces Cervical Cancer Cell Apoptosis

The morphological changes occurring during cell death were observed under a normal inverted microscope. HeLa cells were induced to apoptosis accompanied by shrinkage of cells and membrane blebbing after treatment with 10 mg/ml Cv-AP for 7 hours, Propidium iodide (PI) was added at the beginning as a marker for cell death (FIGS. 8A-8D).

Cv-AP induced cell death was quantified using PI staining and examined using fluorescence microscope. In the last stage of apoptosis, which happens after membrane blebbing and nuclear chromatin condensation, PI can pass through the membrane and bind denatured DNA. Based on counting HeLa cells treated with different concentration of root extract together with untreated HeLa cells as negative control a LD50 was calculated (FIGS. 8A-8D).

It was considered important to ascertain whether the death of the HeLa cells was through activation of an apoptotic pathway. The expression of apoptotic related protein cleaved caspase-3 was examined by immunofluorescence staining. Cleaved caspase-3 was expressed in almost all the HeLa cells after treatment with the Cv-AP at 10 mg/ml. In sharp contrast very little cleaved caspase-3 was expressed in untreated HeLa cells (FIGS. 8A-8D).

Example 7

*Clerodendrum viscosum* Extract does not Affect Primary Human Fibroblast Cells

Both HeLa cells and normal primary human fibroblast cells were seeded at a density of 5,000 cells per well in 96-well plates and incubated for 24 hours for attachment. Cv-AP (10 mg/ml) was added and the cells were incubated at 37° C., with 5% $CO_2$ for 8 hours. Propidium iodide (PI) was added as a marker for death of the cells. Apoptosis occurred in most HeLa cells accompanied with shrinkage and blebbing (FIGS. 8A-8D). Most of the HeLa cells were stained by PI, which indicates that the Cv-AP induced apoptosis of HeLa cells. However, most of the human primary fibroblast cells maintained their cells shape and survived (FIGS. 8A-8D). This implies that Cv-AP is selectively toxic to cancer cells.

Example 8

Bioassay Guided Purification of *Clerodendrum viscosum* Root Extracts

Cv-AP, obtained as previously described, is redissolved in 0.1 M ammonium bicarbonate, and further fractioned into 4 subfractions by size exclusion column chromatography using a GE Healthcare HiPrep Superdex 200 300/10 size exclusion column. See FIGS. 2A-2D. For each fractions, MTT (3-[4,5-dimethylthiazol-2-yl]-2,5 diphenyl tetrazolium bromide) assay, as described above, was used to determine its bioactivity. Fraction 3 was further purified by a series of precipitation steps as described in FIG. 2A.

TABLE 1

Summary of the inhibitory bioactivity of the isolated fractions shown in FIG. 2.

| | IC50 (mg/ml) | Specific activity* | Yield percent | Total activity |
|---|---|---|---|---|
| Formula 4 | 0.921 | 1 | 1 | 1 |
| p1 | | | 2.67% | |
| p2 | 2.828 | 0.325672 | 8.27% | 0.026933% |
| p3 | 0.15 | 6.14 | 28.99% | 1.779986% |
| p4 | 0.439 | 2.09795 | 11.67% | 0.244831% |
| HP3 | 0.12 | 7.675 | 19.69% | 151.12% |
| ESHP3 | 1.12 | 0.822 | 14.47% | 11.90% |
| EPHP3 | 0.03 | 30.7 | 2.87% | 88.11% |

*the unit of the activity is IC50 of formula 4.

Example 9

Cytotoxicity of Cv-AP Across Several Cervical Cancer Lines

Applicants tested the cytotoxicity of the composition as described above across several cervical cancer cell lines using the MTT assay. The cytotoxicity as represented by IC 50 is summarized in Table 2.

TABLE 2

Cytotoxicity of the different cervical cancer lines

| | HeLa (IC50, mg/ml) | Siha (IC50, mg/ml) | me180 (IC50, mg/ml) | caski (IC50, mg/ml) | c33a (IC50, mg/ml) | Ms51 (IC50, mg/ml) |
|---|---|---|---|---|---|---|
| 1 | 9.2 | 5.6 | 4.7 | 2.5 | 2.4 | 3.7 |
| 2 | 6.7 | 5.4 | 4.1 | 3.2 | 2.8 | 4.2 |
| 3 | 5.8 | 5.5 | 4.8 | 4.6 | 3.5 | 4.6 |
| 4 | 5.8 | 8.7 | 5.1 | 4.7 | 2.8 | 4.5 |
| 5 | 6.7 | 7.8 | 5.5 | 3.3 | 1.8 | 4.4 |
| 6 | | 6.7 | 6.1 | 4.2 | 1.4 | 3.9 |
| Median | 6.84 | 6.6 | 4.84 | 3.66 | 2.66 | 4.28 |
| Standard Deviation | 1.39 | 1.54 | 0.51 | 0.95 | 0.62 | 0.35 |
| Standard Variance | 1.94 | 2.37 | 0.26 | 0.91 | 0.38 | 0.12 |

The invention claimed is:

1. A method of inhibiting cervical cancer cell proliferation, said method comprising contacting said cell with an effective amount of a composition comprising an aqueous protein extract of *Clerodendrum viscosum* root; wherein the extract comprises a glycoprotein having a molecular weight of about 25 kDa as determined by MALDI-TOF; and induces caspase-3 activation.

2. The method according to claim 1, wherein the glycoprotein comprises a terminal α-D-mannosyl group.

3. The method according to claim 1, wherein the glycoprotein comprises a terminal α-D-glucosyl group.

4. The method according to claim 1, wherein the extract induces apoptosis of cancer cells.

5. The method according to claim 1, wherein the method further comprises administering a chemotherapeutic agent to the cervical cancer cells.

6. The method according to claim 1, wherein the composition comprises at least one pharmaceutically acceptable carrier.

7. The method according to claim 1, wherein the MALDI-TOF data comprises m/z peaks at about 6.9 kDa, about 9.2 kDa, about 13.5 kDa, and about 25 kDa.

* * * * *